(12) United States Patent
Wieczorek et al.

(10) Patent No.: US 6,292,528 B1
(45) Date of Patent: Sep. 18, 2001

(54) COMPUTER TOMOGRAPH DETECTOR

(75) Inventors: Herfried Wieczorek, Aachen; Josef Lauter, Geilenkirchen; Stefan Schneider, Aachen, all of (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/428,770

(22) Filed: Oct. 28, 1999

(30) Foreign Application Priority Data

Oct. 28, 1998 (EP) .................................. 98203651

(51) Int. Cl.$^7$ ...................................... A61B 6/00
(52) U.S. Cl. ................ 378/19; 378/98.2; 250/370.09; 250/363.2; 250/367
(58) Field of Search ................ 378/19, 4, 98.2; 250/370.01, 370.09, 363.2, 367

(56) References Cited

U.S. PATENT DOCUMENTS

| | | | |
|---|---|---|---|
| 4,739,521 | * | 4/1988 | Akimoto . |
| 5,084,639 | | 1/1992 | Ribner ................................. 307/490 |
| 5,291,402 | | 3/1994 | Pfoh ................................. 364/413.14 |
| 5,500,534 | * | 3/1996 | Robinson et al. . |
| 5,886,353 | * | 3/1999 | Spivey et al. ................... 250/370.09 |

FOREIGN PATENT DOCUMENTS

| | | | |
|---|---|---|---|
| P0715830 | 6/1996 | (EP) | ................................. A61B/6/03 |
| 0819406 | 1/1998 | (EP) | ................................. A61B/6/03 |

OTHER PUBLICATIONS

"Computed tomography scanning with simultaneous patient translation" by Carl. R. Crawford and Keving F. King, in Med. Phys. 17(6), Nov./Dec. 1990.

* cited by examiner

*Primary Examiner*—Robert H. Kim
*Assistant Examiner*—Pamela R. Hobden
(74) *Attorney, Agent, or Firm*—John F. Vodopia

(57) ABSTRACT

A computer tomograph detector for the detection of electromagnetic radiation transmitted by an object, which detector includes at least one detector row which consists of a plurality of detector elements, each detector element including a scintillator for converting radiation of a first energy level into radiation of a second energy level, as well as a photosensor for converting the radiation into an electrical current, each photosensor being associated with an amplifier element, is extended in such a manner that it can include a plurality of detector rows while the electronic noise is nevertheless reduced and at the same time a higher DQE is obtained; this is achieved by arranging a plurality of photosensors and the associated amplifier elements on the same substrate in integrated semiconductor technique.

18 Claims, 3 Drawing Sheets

COMPUTER TOMOGRAPH DETECTOR

BACKGROUND OF THE INVENTION

1. Field of the Invention

The invention relates to a computer tomograph detector for the detection of electromagnetic radiation transmitted by an object, which detector includes at least one detector row which consists of a plurality of detector elements, each detector element including a scintillator for converting radiation of a first energy level into radiation of a second energy level, as well as a photosensor for converting the radiation into an electrical current, an amplifier element being associated with each photosensor.

2. Description of Related Art

Computer tomographs serve to form planar images of imaginary slices of an object, for example a body. A computer tomograph generally consists of a circular portal frame or gantry in which a scanning device with an X-ray source is integrated. The scanning device rotates about an imaginary longitudinal axis extending through the body. After having traversed the body, the X-rays are incident on an oppositely situated detector which rotates together with the scanning device. The reconstruction of a single image requires a set of images which correspond to different protection angles, each image having radiation intensities which are detected by individual detector elements.

Detectors comprising one or more rows are known. EP 0 819 406 A1 discloses a computer tomograph with a plurality of parallel detector rows, i.e. a so-called multi-line detector. The detector consists of a two-dimensional array of detector elements, i.e. a plurality of detector rows, which are arranged parallel to one another in the direction of the axis of rotation (z direction). A multi-line detector offers the advantage that during a rotation of the gantry a plurality of cross-sectional images can be simultaneously picked up in dependence on the extent of the detector in the z direction.

In the case of a computer tomograph with a one-dimensional detector, i.e. single-line detector, only the cross-sectional image of a fan-shaped beam is picked up. In order to obtain a volume image, the body, i.e. the patient, must be moved through the computer tomograph. When a multi-line detector is used, however, a pyramid-like beam or cone beam is used, so that a volume image can be picked up already during a single rotation of the gantry, said volume image consisting of a number of cross-sectional images in conformity with the number of rows of the array.

The body is scanned helically or spirally in the case of single-line detectors as well as in the case of multi-line detectors. The gantry is then rotated about the body while at the same time the patient is moved along the axis of rotation relative to the gantry. Using a multi-line detector, the execution of such a spiral scan is significantly faster than when use is made of a single-line detector, because the patient can be transported over the full width of the detector during one revolution of the gantry. Such a reduction of the scanning time by using multi-line detectors minimizes the detrimental image artefacts due to motions of the patient, for example due to respiration or muscle contractions.

The multi-line detector which is known from EP 0 819 406 A1 concerns a two-dimensional array of detector elements, each of which is constructed on the basis of a ceramic scintillator which is succeeded by a photodiode. The detector signals are received by a multiplexer. The multiplexer applies the information to a computer and the images of the body are displayed on a monitor.

A computer tomograph provided with a two-dimensional array is also known from U.S. Pat. No. 5,291,402. As is customary in detectors of this kind, each detector element of the detector array is electrically independent. The signals of the decoupled detector elements are acquired by means of a data acquisition system. Those skilled in the art will know that such a data acquisition system requires a multitude of discrete amplifier elements which are associated with the individual detector elements.

It is a drawback that the relevant photodiodes are connected to the amplifier elements via individual supply leads. This leads to a very large number of connections, notably in the case of multi-line detectors. The high density of the connection leads may lead to crosstalk of the channels and irritations due to the coupling in of interference by capacitive and/or inductive coupling. This causes a high, undesirable electrical noise and a deterioration of the DQE (Detective Quantum Efficiency).

Citation of a reference herein, or throughout this specification, is not to construed as an admission that such reference is prior art to the Applicant's invention of the invention subsequently claimed.

Therefore, it is an object of the invention to provide a computer tomograph detector which may comprise a plurality of detector rows, involves less electronic noise and at the same time offers a higher DQE and fast preparation of the desired image.

SUMMARY OF THE INVENTION

This object is achieved by means of a detector comprising: at least one detector row which further comprises a plurality of detector elements, each detector element including a scintillator for converting radiation of a first energy level into radiation of a second energy level, as well as a photosensor for converting the radiation into an electrical current, and an amplifier element which is associated with each photosensor, wherein a plurality of photosensors and the associated amplifier elements are arranged on the same substrate in an integrated semiconductor technique. Advantageous embodiments of the invention are disclosed in the dependent claims.

The photosensors and amplifier elements constructed in semiconductor technology, notably in standard CMOS technology, and arranged on the same substrate enable minimization of the configuration of leads for the high impedance signals between the photosensors and amplifier elements; such a configuration of leads can hardly be realized at acceptable costs in customary multi-line detectors. As a result of the minimization of the stretch of leads, the parasitic line capacitances can also be reduced to a minimum. This results in a reduction of the electrical noise and the susceptibility to interference, but the DQE remains high.

The faster preparation of the patient image makes it easier to work with such a computer tomograph and image artefacts are avoided due to the fast composition of the images.

Preferably, the detector chip is made using CMOS technology. However, other semiconductor technologies are also feasible, for example the bipolar technique or JFET technology (JFET=Junction Field Effect Transistor). The CMOS technique offers advantages in respect of cost, low current consumption, availability as well as the realization of logic circuit components. Process technologies such as bi-CMOS, (HV-CMOS), NMOS or PMOS are feasible.

Preferably, the detector consists of an array, i.e. a two-dimensional surface, of detector elements.

It is feasible to arrange the entire array of the detector elements on a single substrate., The array is customarily composed of a plurality of chips.

Each photosensor and the associated amplifier element in a first embodiment of the detector are arranged so as to be adjacent. In a second embodiment the amplifier elements are arranged at a distance from the photosensors, for example at the edge of a chip.

Each detector element includes a scintillator for converting the electromagnetic radiation, i.e. X-rays, into radiation of a different energy level. The scintillator is preferably constructed as a matrix of scintillator elements. The scintillator elements consist either of monocrystals or of a plurality of crystals. For example, a scintillator consists of cadmium tungstate $(CdWO)_4$ or of $Gd_2O_2S:Pr, F, Ce)$.

In order to shield the sensitive amplifier elements from the electromagnetic radiation, there are provided shielding layers which reduce the radiation load on the electronic components, notably on the gate oxide.

In the first embodiment, i.e. the embodiment with the adjacently arranged photosensor and amplifier element, for this purpose absorber layers are provided between the scintillator elements, which absorber layers extend vertically relative to the surface of the scintillator. In order to shield the sensitive amplifier elements from the electromagnetic radiation, the amplifier elements are provided directly underneath the absorber layers.

The absorber layers are also referred to as spacers or separators. They prevent crosstalk between the individual detector elements in that the photons are reflected back to the scintillator element on the separators and fluorescence X-ray quanta (K-escape quanta) are absorbed. These absorber layers preferably concern fillings of a heavy metal or heavy metal alloys, for example of tantalum, tungsten, lead or bismuth. These fillings can be realized, for example by inserting metal foils, by pouring liquid metals or by sedimentation of heavy metal salts.

In order to enhance the reflection on the absorber layers, the surface thereof is preferably provided with a reflecting layer.

In the second embodiment, i.e. the embodiment in which the amplifier elements are arranged at the edge of the substrate, the amplifier elements are shielded from the electromagnetic radiation by means of metal plates.

The amplifier elements used for the computer tomograph detector must satisfy the typical requirements in respect of a large dynamic range of from 18 to 20 bits and at the same time a high linearity. The signal to be processed is a photocurrent which is integrated and converted into an analog output voltage within the frame time.

Such requirements are satisfied, for example by charge-sensitive, capacitively fed back or transimpedance amplifiers. In the capacitively fed back amplifiers the charge integration is performed on a feedback capacitance which is digitally erased after each integration interval. Transimpedance amplifiers or current amplifiers also operate with a feedback capacitance which integrates the photocurrent. The discharging or resetting, however, is not realized by digital erasure but continuously in time.

Other types of amplifier, operating without feedback, for example source follower circuits, usually are not suitable for computer tomograph detectors since they do not satisfy the requirements in respect of linearity and dynamic range.

The outputs of the amplifier elements are connected to a multiplexer for the processing of the signals, said multiplexer combining the outputs of the amplifiers. Alternatively, switching transistors are also feasible. The multiplexer is succeeded by an analog-to-digital converter whose digital signals are applied to an arithmetic unit. Alternatively, an analog-to-digital converter whose output signals are digitally multiplexed can be assigned to each individual amplifier.

Preferably, each multiplexer and/or analog-to-digital converter is arranged on the same substrate with the detector elements. The off-chip operations are thus minimized. The possibility of purely digital interfaces notably enables direct connection of the chips to a data bus. This has a positive effect on the suppression of the coupling-in of interference.

The photosensors used in the computer tomograph detector according to the invention are preferably photodiodes. Phototransistors are also feasible. It is advisable to use integrative semiconductor technologies in crystalline silicon, because photosensors having short response times can thus be realized.

BRIEF DESCRIPTION OF THE DRAWINGS

Further details and advantages of the invention will become apparent following description of the embodiments of the invention which are shown in the Figures. Therein.

DETAILED DESCRIPTION OF THE PREFERRED EMBODIMENT

Figure 1:
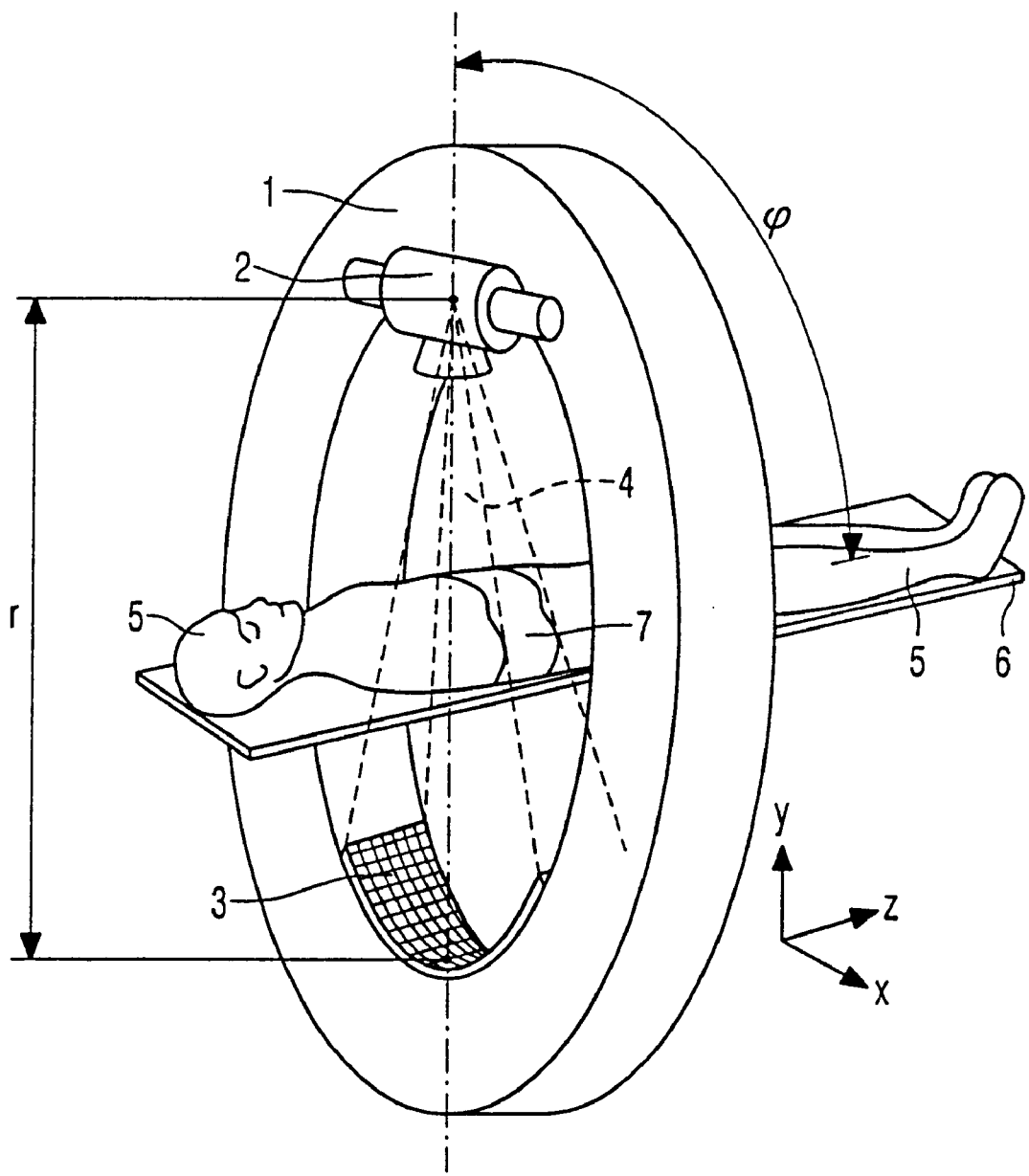
FIG. 1 shows diagrammatically a computer tomograph with a multi-line detector.

FIG.1 shows diagrammatically a computer tomograph with a multi-line detector. The X-ray tube 2 as well as the facing multi-line detector 3 are mounted in a circular portal frame or gantry 1. The X-ray tube 2 projects a cone-shaped X-ray beam 4 through the patient 5 and onto the multi-line detector 3. The patient 5 to be examined is transported through the rotating gantry 1 on a table 6.

The detector array 3 is arranged at a distance r from the focus of the X-ray tube 2. During a complete revolution of the gantry 1, the X-ray beam 4 irradiates the patient 5 in the gantry plane from different directions φ relative to the normal. A cross-sectional image 7 of the patient in the irradiated zone is calculated by means of these projections.

The detector array 3 is composed of a plurality of detector elements which are arranged in a plurality of rows. These rows extend in parallel in the direction of the axis of rotation (z direction).

Figure 2:
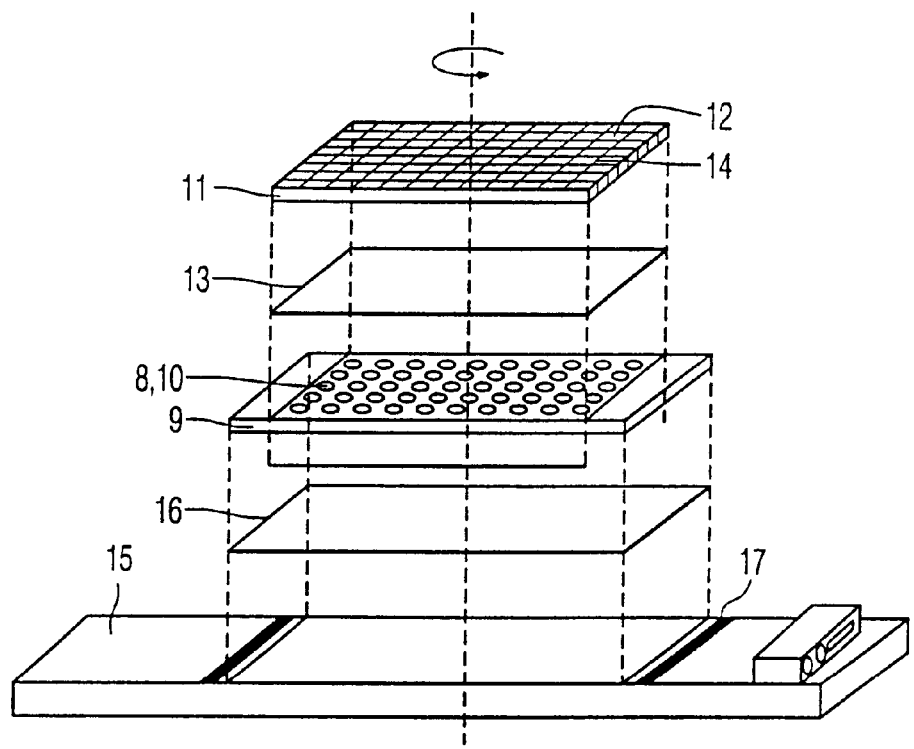
FIG. 2 is an exploded view of a CMOS chip with a plurality of detector elements.

FIG. 2 is an exploded view of the construction of a CMOS substrate according to the invention with a plurality of detector elements. A plurality of photodiodes 8 (graphically accentuated in white) and the associated amplifier elements (not shown) are realized in an integrated semiconductor technique on the same substrate. Thus, a CMOS chip 9 is realized on which the detector elements 10 (also referred to as pixels or picture elements) are arranged in the form of a matrix; for example, in this case they are arranged in six rows in the longitudinal direction and in nine columns in the transverse direction. A complete detector array 3 customarily consists of a plurality of consecutively arranged chips 9.

Over each CMOS chip 9 there is arranged a scintillator 11 which is as large as the CMOS chip 9 and consists of a matrix of scintillator crystals 12. The scintillator 11, formed by individual $CdWO_4$ crystals 12, is connected to the CMOS chip so as to be exactly positioned with respect thereto by means of a thin layer of an optical adhesive 13. Absorber layers 14 which will be described in detail hereinafter are provided between the individual crystals 12 of the scintillator.

The CMOS chips 9 are attached to a printed circuit board or PCB 15 by means of an adhesive layer 16. The electrical connections from the CMOS chip 9 to the PCB 15 are formed by leads to the bond pads 17.

Figure 3:
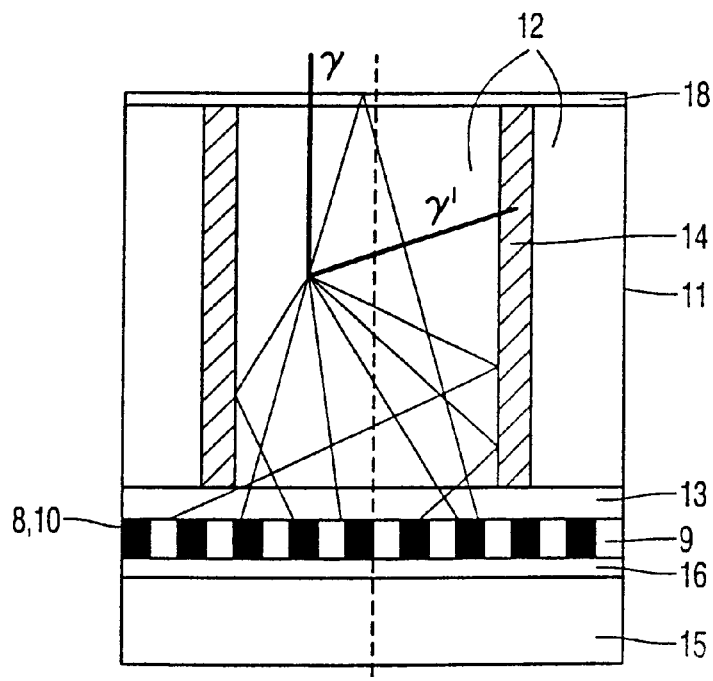
FIG. 3 is a cross-sectional view of a plurality of detector elements in CMOS technology.

FIG. 3 partly shows the cross-section of the CMOS chip 9 with the scintillator 11. This Figure shows how the photodiodes 8 are provided on the substrate of the CMOS chip Over the scintillator 11 there is provided a reflection layer 18 which is not shown in FIG. 2. The absorber layers 14 can be seen in the vertical direction between the individual crystals 12.

When the detector is exposed to X-rays, the X-ray quanta ($\gamma$) are absorbed in the scintillator 11 and converted into visible light (diagrammatically represented by black strokes). These photons are reflected partly on the absorber layers 14 or on the reflecting layer 18 provided on the scintillator and are subsequently absorbed in the CMOS chip 9 bonded to the scintillator 11. Secondary X-ray quanta ($\gamma'$) are absorbed in the absorber layers 14 in order to avoid crosstalk between neighboring detector elements.

The photons absorbed in the photodiodes 8 situated underneath the scintillator crystals 12 generate electron hole pairs. The charge thus generated is collected element-wise in the amplifier elements (not shown) which are arranged directly underneath the absorber layers 14 in order to protect the sensitive circuits from the X-rays.

The outputs of the amplifier elements are connected to a multiplexer which is not shown. The signals are transferred to the edge of the CMOS chip, via appropriate read-out lines, and applied to an arithmetic unit by way of an analog-to-digital converter.

Figure 4:
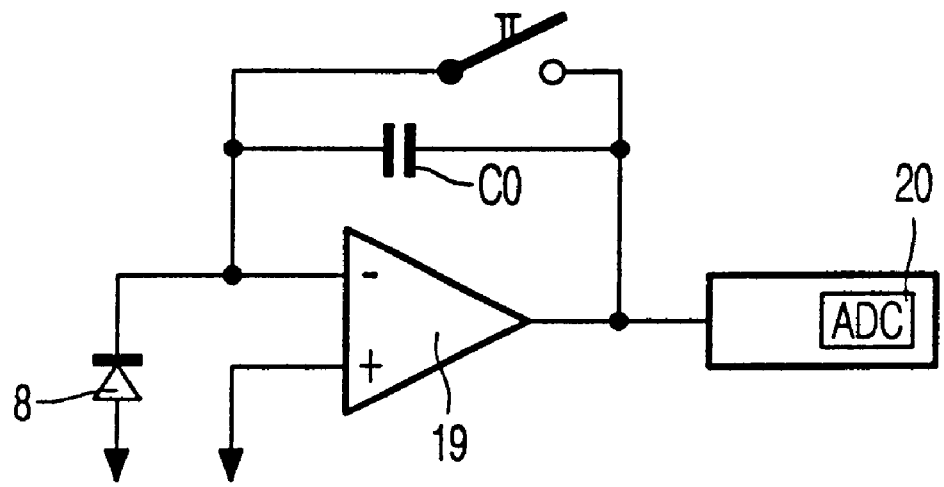
FIG. 4 shows a circuit diagram of a charge-sensitive amplifier element for use in a computer tomograph detector according to the invention.
Figure 5:
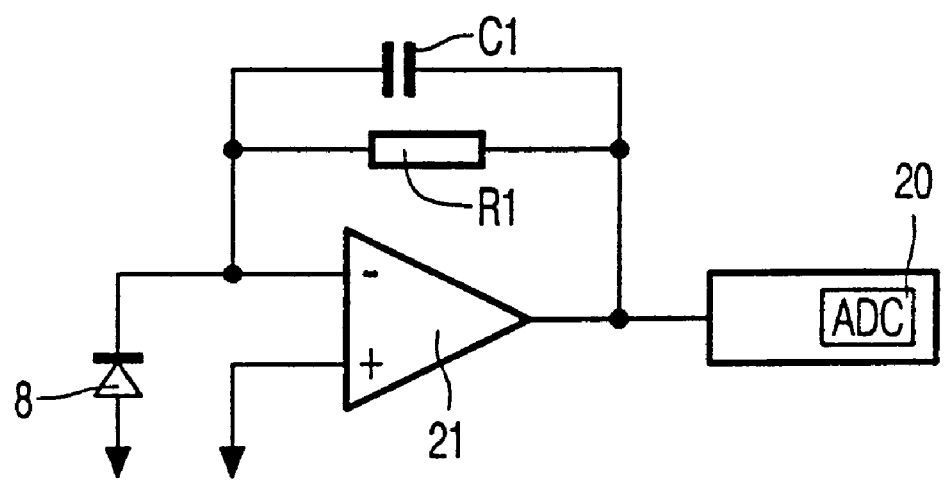
FIG. 5 shows a circuit diagram of a current-sensitive amplifier element for use in a computer tomograph detector according to the invention.

The FIGS. 4 and 5 show circuit diagrams of two different types of amplifier which are suitable for use in the detector according to the invention.

The first type concerns a charge-sensitive amplifier 19 with digital reset. Amplifiers of this kind operate as charge integrators. The charge integration is performed via a feedback capacitance C0 which is digitally erased after each integration interval (FIG. 4) The output signal of the amplifier element is a voltage signal which is proportional to the charge quantity generated and reciprocal to the selected feedback capacitance. The voltage signal is applied to an analog-to-digital converter (20).

The transimpedance amplifier or current amplifier 21 shown in FIG. 5 also operates with a feedback capacitance C1 which integrates the photocurrent. The discharging or resetting, however, is not performed by digital erasure but time continuously via a resistor R1 connected parallel to the feedback capacitance C1. The output voltage is approximately proportional to the charge integral of the photocurrent. The voltage signal is applied to an analog-to-digital converter 20 and further to an arithmetic unit.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A computer tomograph detector for the detection of electromagnetic radiation transmitted by an object including at least one detector row, the detector row further comprising:

a plurality of detector elements, each detector element including a scintillator for converting radiation of a first energy level into radiation of a second energy level, as well as a photosensor for converting the radiation into an electrical current, and a plurality of amplifier elements, an amplifier element being associated with each photosensor, wherein a plurality of photosensors and the associated amplifier elements are arranged on the same substrate in an integrated semiconductor technique.

2. A detector as claimed in claim 1 wherein the integrated semiconductor technique is standard CMOS technique.

3. A detector as claimed in claim 1 wherein each photosensor and the associated amplifier element are arranged so as to be adjacent.

4. A detector as claimed in claim 1 wherein the amplifier elements are arranged at the edge of the substrate at a distance from the photosensors.

5. A detector as claimed in claim 1 wherein the scintillator further comprises a plurality of scintillator elements.

6. A detector as claimed in claim 5 further comprising absorber layers which extend in the vertical direction relative to the surface of the scintillator and are provided between the scintillator elements.

7. A detector as claimed in claim 6 wherein the amplifier elements are arranged directly underneath the absorber layers.

8. A detector as claimed in claim 4 characterized in that further comprising metal plates provided at the edge of the substrate, wherein the amplifier elements are arranged underneath these metal plates.

9. A detector as claimed in claim 1 wherein the scintillator is connected to the chip by way of an optical adhesive.

10. A detector as claimed in claim 1 wherein the amplifier elements are constructed as charge-sensitive, capacitively fed back amplifiers.

11. A detector as claimed in claim 1 wherein the amplifier elements are transimpedance amplifiers which are fed back via a respective capacitance and a resistor connected parallel to the capacitance.

12. A detector as claimed in claim 1 wherein the outputs of the amplifier elements are connected to at least one multiplexer, each multiplexer being succeeded by an analog-to-digital converter whose digital signals are applied to an arithmetic unit.

13. A detector as claimed claim 1 wherein each amplifier element is succeeded by an analog-to-digital converter whose digital signals are applied to an arithmetic unit via a multiplexer or a bus.

14. A detector as claimed in claim 12 wherein each multiplexer and analog-to-digital converter is arranged on the same substrate as the detector elements.

15. A detector as claimed in claim 1 wherein the photosensor is a photodiode.

16. A computer tomograph comprising:

an X-ray source for emitting an X-ray beam, the X-ray beam being rotatable about a system axis, a detector as claimed in claim 1 which is struck by the X-ray beam, and an arithmetic unit for calculating images of the object examined on the basis of the detector signals formed during the various projections.

17. A computer tomograph as claimed in claim 16 wherein the detector further comprises a two-dimensional array of detector elements of n rows and m columns, n and m being natural numbers larger than 1.

18. The detector of claim 13 wherein each analog-to-digital converter is arranged on the same substrate as the detector elements.

* * * * *